US00PP10067P

United States Patent [19]

Hamby

[11] Patent Number: Plant 10,067

[45] Date of Patent: Oct. 14, 1997

[54] PHLOX PLANT NAMED 'LAUREL BETH'

[75] Inventor: Michael David Hamby, McMinnville, Tenn.

[73] Assignee: Mary's Greenhouse, Inc., McMinnville, Tenn.

[21] Appl. No.: 677,894

[22] Filed: Jul. 10, 1996

[51] Int. Cl.[6] ..... A01H 5/00

[52] U.S. Cl. ..... Plt./87.7

[58] Field of Search ..... Plt./87.7

*Primary Examiner*—James R. Feyrer

*Attorney, Agent, or Firm*—C. A. Whealy

[57] ABSTRACT

A distinctive cultivar of Phlox plant named 'Laurel Beth', characterized by its variegated leaves with green centers and distinct white leaf margins; white leaf margin that is tinged with dark rose coloration during cool temperatures; dark rose stem coloration during cool temperatures; and rose red apices during the early spring.

1 Drawing Sheet

The present invention relates to a new and distinct cultivar 'Creeping Phlox, botanically known as *Phlox subulata*, and reinafter referred to by the cultivar name Laurel Beth.

The new cultivar is a foliage color mutation from the npatented *Phlox subulata* cultivar Star Red. The new ltivar was discovered by the inventor in a controlled vironment in McMinnville, Tenn., within a population of ants of the cultivar Star Red.

In side-by-side comparisons in McMinnville, Tenn. under mmercial practice, plants of the new Phlox are similar to ants of the cultivar Star Red in flower color and plant habit. owever plants of the cultivar Star Red have solid green ves whereas plants of the new Phlox have variegated ves.

Asexual reproduction of the new cultivar by leaf cuttings ken at McMinnville, Tenn. has shown that the unique tures of this new Phlox plant are stable and reproduced e to type in successive generations of asexual reproduc-n.

The following traits have been repeatedly observed and determined to be the unique characteristics of 'Laurel th'. These characteristics in combination distinguish the w Phlox plant as a new and distinct cultivar:

1. Variegated leaves with green centers and distinct white f margins.
2. White leaf margin that is tinged with dark rose colora-n during cool temperatures of fall through early spring.
3. Dark rose stem coloration during cool temperatures of l through early spring.
4. Rose red apices during the early spring.

The new Phlox plant has not been observed under all ssible environmental conditions. The phenotype may vary nificantly with variations in environment such as tem-rature and light level, without, however, any variance in notype.

BRIEF DESCRIPTION OF THE FIGURES OF THE DRAWING

The accompanying colored photographs illustrate the rall appearance of the new cultivar, showing the colors as as it is reasonably possible to obtain in colored repro-tions of this type. In the drawing

Figure 1:
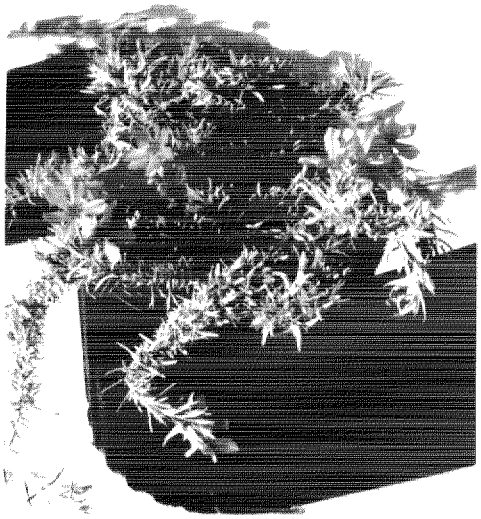
FIG. 1 is a top perspective view of a typical potted cimen of 'Laurel Beth'.
Figure 2:
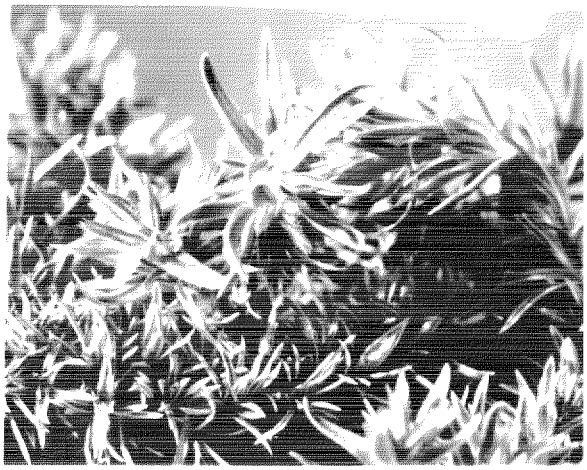
FIG. 2 comprises a side perspective view of typical age of 'Laurel Beth' after exposure to cool temperatures.
Figure 3:
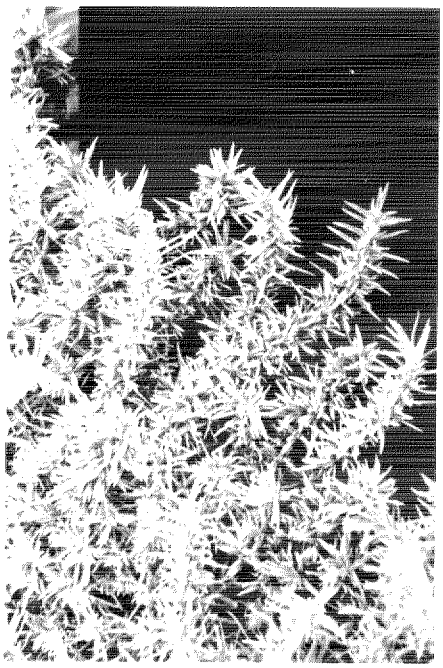
FIG. 3 shows, in side perspective view, the foliage of specimens of 'Laurel Beth' after exposure to warm temperatures; and, FIG. 4 illustrates, in close-up view, a typical flower of 'Laurel Beth'.
Figure 4:
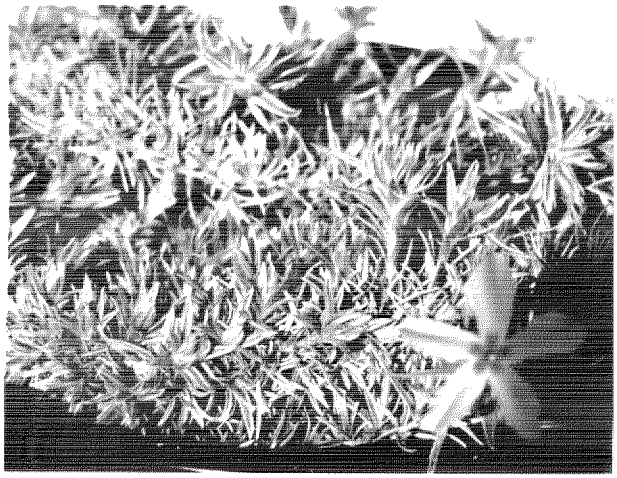

Flower and foliage colors in the photographs may appear different from the actual colors due to light reflectance.

The following observations, measurements, values, and comparisons describe plants grown in McMinnville, Tenn., and Roanoke, Tex., in production fields and 1-gallon containers, respectively.

In the following description, color references are made to The Royal Horticultural Society Colour Chart except where general terms of ordinary dictionary significance are used.

Classification:

*Botanical.*—*Phlox subulata* cultivar Laurel Beth.

*Commercial.*—Creeping Phlox.

Parentage: Naturally occurring foliage color mutation of *Phlox subulata* cultivar Star Red (not patented).

Propagation:

*Type.*—By cuttings or by division.

*Time to develop roots.*—21 days at temperatures of 25° C.

*Rooting habit.*—Vigorous, fibrous, and well-branched.

Plant Description:

*Plant form and growth habit.*—Perennial, mounded, spreading and prostrate. Used as a groundcover, border plant, and in rock gardens.

*Vigor.*—Vigorous.

*Growth rate.*—Moderate to high, usually 12 to 16 weeks to produce a finished 1-gallon container from an unrooted cutting.

*Branching habit.*—Freely branching, dense plants.

*Height, soil level to top of leaves.*—About 10 cm.

*Height, soil level to top of flowers.*—About 15 cm.

*Stem color.*—Fall through early spring: Dark rose. Spring through early fall: Grayed green.

Foliage description:

*Arrangement.*—Opposite.

*Leaf appearance.*—Leathery.

*Leaf size, largest leaves.*—Length: About 2 cm. Width: About 2 mm.

*Leaf shape.*—Narrow, linear.

*Leaf tip.*—Acuminate.

*Margin type.*—Entire.

*Leaf surface.*—Folded upright lengthwise, in cross-section, V-shaped.

*Texture.*—Glabrous.

*Petiole.*—Sessile.

*Color.*—Center, abaxial: 137B. Margin, abaxial: 155D. Center, adaxial: 137C. Margin, adaxial: 155D. Margin, cool temperatures, fall through early spring: 61A.

Flower description:

*Natural flowering season.*—Early to mid spring. Plants may flower during the summer as well.

*Flower arrangement.*—Single flowers arranged in umbels, flowers held upright and above the foliage.

*Flower appearance.*—Fused corolla with five petals. Rose pink with red purple eye and midveins. Not persistent.

*Fragrance.*—Slight.

*Flower diameter.*—About 5 cm.

*Flower depth(height).*—About 5 mm.

*petals.*—Appearance: Velvety, satiny. Texture: Smooth. Arrangement: Five fused into a corolla, not overlapping. Shape: Oblong. Margin: Entire. Surface: Usually flat or slightly twisted. Tip: Rounded. Size: Length: About 2.5 cm. Width: About 1.25 cm. Color: Abaxial: 68A. Midvein and base: 61B. Adaxial: 75A.

Disease resistance: Under commercial conditions, resistance or susceptibility to pathogens has not been observed.

Seed production: Seed production is rarely observed.

It is claimed:

1. A new and distinct Phlox plant named 'Laurel Beth', as illustrated and described.

* * * * *